US008652532B2

(12) United States Patent
Courtois et al.

(10) Patent No.: US 8,652,532 B2
(45) Date of Patent: Feb. 18, 2014

(54) FOOD COMPOSITION COMPRISING GLUCOSAMINE

(75) Inventors: Didier Courtois, St. Avertin (FR); Stephane Michaux, Monnaie (FR); Vincent Petiard, Tours (FR); Andre Touche, Monts (FR)

(73) Assignee: Nestec S.A., Vevey (CH)

( * ) Notice: Subject to any disclaimer, the term of this patent is extended or adjusted under 35 U.S.C. 154(b) by 71 days.

(21) Appl. No.: 10/595,894

(22) PCT Filed: Nov. 19, 2004

(86) PCT No.: PCT/EP2004/013184
§ 371 (c)(1), (2), (4) Date: Jul. 24, 2006

(87) PCT Pub. No.: WO2005/053710
PCT Pub. Date: Jun. 16, 2005

(65) Prior Publication Data
US 2007/0141018 A1    Jun. 21, 2007

(30) Foreign Application Priority Data
Nov. 21, 2003   (EP) .................................. 03026498

(51) Int. Cl.
*A61K 36/00*    (2006.01)

(52) U.S. Cl.
USPC ....................................................... 424/725

(58) Field of Classification Search
None
See application file for complete search history.

(56) References Cited

U.S. PATENT DOCUMENTS

| | | | |
|---|---|---|---|
| 4,086,368 A * | 4/1978 | Bosley et al. | 426/464 |
| 4,855,137 A | 8/1989 | Keri et al. | |
| 4,871,574 A | 10/1989 | Yamazaki et al. | |
| 4,938,974 A * | 7/1990 | Bichsel et al. | 426/74 |
| 5,141,964 A * | 8/1992 | Noel | 514/777 |
| 5,916,622 A * | 6/1999 | Ecochard | 426/596 |
| 6,420,350 B1 * | 7/2002 | Fleischner | 514/62 |
| 2002/0099032 A1 * | 7/2002 | Higashi et al. | 514/62 |
| 2004/0001898 A1 | 1/2004 | Malnoe et al. | |

FOREIGN PATENT DOCUMENTS

| | | |
|---|---|---|
| EP | 0850569 | 7/1998 |
| EP | 1325682 | 7/2003 |
| HU | 66929 | 1/1995 |
| JP | 01102092 | 4/1989 |
| JP | 02174790 | 7/1990 |
| WO | WO03070168 | 8/2003 |

OTHER PUBLICATIONS

Weichmann. Increase in the Sucrose Content of Sugar Beets After Their Removal From Soil. Sugar. 1917. 19. Abstract.*
Beet. Retrieved from the internet. <http://en.wikipedia.org/wiki/Beets>. Retrieved on Jan. 24, 2011. pp. 1-7.*
Wikipedia.org. Retrieved from the internet on Nov. 20, 2011. <http://en.wikipedia.org/wiki/Carrot>. 2 pages.*
Kanto. Proceeding of the World Congress on Vegetable Protein Utilization in Human Foods and Animal Feedstuffs. The American Oil Chemists Society, Jul. 1, 1989.*
Doyt, L.C. et al., "Alternative Treatments and Rheumatic Diseases," Bulletin on the Rheumatic Diseases, vol. 48, No. 7, (1999).
The Written Opinion of the International Searching Authority, Nov. 27, 2006.

* cited by examiner

*Primary Examiner* — Amy L Clark
(74) *Attorney, Agent, or Firm* — K&L Gates LLP

(57) ABSTRACT

The present invention relates to an orally ingestible food or pet food composition or cosmetic composition containing glucosamine generated from plant materials through a drying process for the maintenance of joint health or prevention, alleviation and/or treatment of osteoarthritis, or the improvement of the skin quality and prevention or restoration of age-related alterations of skin. It also relates to the use of the composition in the manufacture of a nutritional product, a supplement, a treat, a medicament or a cosmetic product and methods for the maintenance of bone health, prevention, alleviation and/or treatment of osteoarthritis, improvement of the skin quality and prevention or restoration of age-related alterations of skin which comprises administering an effective amount of the composition.

7 Claims, No Drawings

FOOD COMPOSITION COMPRISING GLUCOSAMINE

The present invention relates to an orally ingestible food or pet food composition or cosmetic composition containing glucosamine generated from plant materials through a drying process. Said food or pet food composition or cosmetic composition is intended for the prevention, alleviation and/or treatment of arthritis and osteoarthritis and/or for improving skin quality and preventing or restoring age-related alterations of skin.

BACKGROUND OF THE INVENTION

Prevention of Osteoarthritis (OA)

From a human perspective, OA is a crippling disease with high socio-economic impact. OA is a heterogeneous group of conditions, including Primary OA (e. g. genitive factors, hormonal factors, mechanical stress to joints) and Secondary OA (e. g. inflammatory episodes, post-traumatic).

It is the leading cause of disability with about 43 million people affected in the US and 240 million worldwide. It has substantial economic impact, e.g. in the US direct treatment costs $ 10.7 billion, indirect costs $ 42.8 billion (missed working days). Symptoms are pain, hypertrophy and stiffness of joints and limitation of movement. Current therapy focuses on pain relief with non-steroidal anti-inflammatory drugs (NSAIDs).

From a pet perspective, osteoarthritis is an age- and weight-related degenerative problem of the joints. It affects 20 Mio dogs worldwide: dogs have trouble in getting up and jumping, are sore after exercise, and/or grumpy. Because of joint degeneration, inflammation sets on.

Natural therapeutic treatments (glucosamine and glycosaminoglycans) are effective in slowing progression of disease.

Use of Glucosamine

The use of pure glucosamine in the treatment of joint diseases is widely described in the patent as well as in the scientific literature, usually in combination with other compounds or extracts from various natural sources. Pure glucosamine is added as glucosamine hydrochloride or glucosamine sulphate, and comes from shellfish hydrolysis. For example, WO20000074696 describes "herbal compositions comprising glucosamine and *Trypterygium wilfordii, Ligustrum lucidum* and/or *Erycibe schmidtii*, for treating inflammation or degeneration of joint tissues, e.g. arthritis" where pure glucosamine is mixed with plant preparation. Other patents relate to compositions of plant carbohydrates as dietary supplements (EP1172041 or EP0923382) where glucosamine is originated from chitin.

The use of glucosamine as an anti-osteoarthritis agent has been intensively developed during the last decade. Glucosamine is suspected to be one of the sole active compound on joint disease such as osteoarthritis (up to recently only symptomatic treatment such as non-steroidal anti-inflammatory drugs have been sought to be efficient).

Glucosamine has also been shown preventing the cartilage degradation by inhibiting the production of MMPs (Matrix metalloproteases) such as MMP1, MMP3 and MMP13

Interestingly glucosamine is also related to the aging process of skin, which has been characterized mainly by the continuous loss of elasticity and the loss of moisture. Skin aging is reflected by major structural changes and variations in composition. Most notably aged skin has less collagen and glycosaminoglycans compared with young skin. Glycosaminoglycan molecules produced by the skin include hyaluronic acid (poly d-glucuronic acid-n-acetyl-d-glucosamine), chondroitin sulfate, and dermatan sulfate. Hyaluronic acid is produced in higher quantities by the skin cells in response to exfoliation. Hyaluronic acid has a large capacity for hydration.

Inhibiting MMP-1 is related to the inhibition of the polyglycan/collagen degradation, and therefore also related to skin ageing: MMP-1 can be induced by UV and is recognized as a marker of the skin ageing. In US2002119107, an invention is based on the selective inhibition of MMP-1 claiming topical compositions for protecting human skin from collagen degradation. US2004037901 claims a regime for inhibiting the adverse signs of effects of cutaneous aging comprising an extract from rosemary plant inhibiting the expression of metalloproteases.

Glucosamine has been shown to significantly improve dryness of the skin and exfoliation. Glucosamine increases the moisture content and improves the smoothness of the skin. These findings suggest that long-term intake of glucosamine is effective in improving moisture content and smoothness of the skin.

It has been shown that oral supplement containing glucosamine lead to a reduction (34%) in the number of visible wrinkles and (34%) in the number of fine lines in a group of women who took the supplement. The use of an oral supplement containing glucosamine, minerals, and various antioxidant compounds can potentially improve the appearance of visible wrinkles and fine lines.

U.S. Pat. No. 6,413,525, describes methods of substantially exfoliating the skin. In particular, the invention relates to topically applied compositions containing an amino sugar in the form of N-acetyl glucosamine: when young skin cells are exposed after exfoliation, they produce larger quantities of hyaluronic acid which is a glycosaminoglycan composed of a chain of alternating, repeating, D-glucuronic acid and N-acetyl-D-glucosamine molecules. N-acetyl-D-glucosamine is known to be a rate-limiting factor in the hyaluronic acid production by living cells. The topical application of glucosamine assists in the continued production of hyaluronic acid.

Other Compositions for topical application containing N-acetyl-D-glucosamine have been also disclosed for example, in JP 59013708 (soften and moisturize the skin) U.S. Pat. No. 5,866,142 (a composition for exfoliating the skin).

Origin of Glucosamine

Glucosamine is an amino monosaccharide found in chitin, glycoproteins, proteoglycans (PGs), and glycosaminoglycans (GAGs) such as hyaluronic acid. Glucosamine is also known as 2-amino-2-deoxyglucose, 2-amino-2-deoxy-beta-D-glucopyranose and chitosamine. It has the following formula:

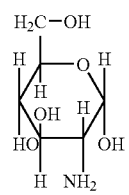

Glucosamine in Animals:

Glucosamine is a constituent of glycosaminoglycans in cartilage matrix and synovial fluids. They are in form of polymers of glucosamine, with an acetyl group attached to a variable number of the individual glucosamine molecules (making them acetylglucosamine).

A polymer composed totally of acetylglucosamine is called chitin, and one composed totally of glucosamine is called chitosan.

The structure of chitin is very similar to cellulose, especially because they both are β (1-4) linked.

The main sources of chitin are the following (in % of total dry matter)

| Fungi | 5-20% | Spiders | 38% |
| Worms | 20-38% | Cockroaches | 35% |
| Squids/Octopus | 3-20% | Water Beetle | 37% |
| Scorpions | 30% | Silk Worm | 44% |
| Edible Crab | 70% | Hermit Crab | 69% |

Glucosamine in Plants:

N-Glycosylproteins, which are N-linked glycoproteins, are present in plants in trace amounts. For example, a glucosamine residue of oligosaccharide is N-glycosidically attached to the amide nitrogen of an asparagine residue of the protein. Examples are phaseolin, legumin, bromelain, laccase, etc. Degradation occurs through the activity of enzymes for de-N-glycosylation (cleavage of glucosamine linkage between N-acetyl-D glucosamine and Asp. residue).

N-Glycosylproteins are different from chitin, found in the extracellular matrix, in the vacuole, associated to membranes (Endoplasmic Reticulum, Golgi, tonoplast, plasma membrane). N-glycans influence the stability, solubility, and biological activity of the protein. De-N-glycosylation seems important during germination and post germinative development.

Such a linked-glucosamine is in limited quantities and not freely available (or through hydrolysis such as strong acidic or enzymatic treatment).

Free glucosamine has not been observed in plant species or only as trace levels: (for examples less than 1 mg/kg dry matter in fresh chicory, carrot, Jerusalem artichoke or beet raw materials, or commercial dried chicory roots such as those from Leroux company (France). The publication of Alabran D. M. and Mabrouk A. F. (Carrot flavor. Sugars and free nitrogenous compounds in fresh carrots, J. Agr. Food Chem., 21 (2), 205-208, 1973) is the only scientific publication describing the presence of free glucosamine in fresh (non-processed, non-dried material) plant material in a relatively high amount (0.071% of fresh carrot). Nevertheless, surprisingly there is no other data reporting free glucosamine on carrot or other plant material in the scientific literature or referenced Nutrition Tables such as "Food Composition and Nutrition Tables, MedPharm (Stuttgart) and CRC Press (Boca Raton), 1994". Furthermore, our own investigation detected less than 1 mg/kg dry matter in commercial root of carrots, and confirm the state of the art in that glucosamine is only present at a level of traces in vegetables. In WO2003/070168, carrot seeds have been studied for their chemical composition and their activity for the reduction of inflammation-related pain, without any reference to glucosamine. It does not concern a food or pet food composition containing glucosamine generated from plant materials through a drying process as set forth in our present invention.

Chicory is used in several food/pet food compositions, using commercial dried, comminuted roots, and usually does not contain significant amount of glucosamine. For example, EP 0850569A1 describes a gelatinised cereal product containing oligosaccharide using chicory root as one of the ingredients. Chicory is used as a source of inulin and fructooligosaccharides and in use the cereal product has a beneficial effect in the gastrointestinal tracts of human and animals. In US2004/0001898A, food compositions, containing chicory, are described for detoxification and cancer prevention.

In EP1325682A1, various plant extracts are used in food or pet food compositions for maintenance of bone health. As in many other food/pet food compositions, using commercial dried, comminuted roots, not containing glucosamine, Chicory is cited only as one of the ingredients of a pet food composition (example 3), not as the ingredient responsible of the claimed biological activity and without any reference to generation of glucosamine or presence or use of glucosamine in plant material or final product or to a specific drying process.

In JP63309147, chicory material is hydrolysed with an acid to generate oligofructosaccharides. It does not refer to glucosamine generation or presence or use of glucosamine in plant material or final product.

In HU66929, a natural fodder additive is described, including oats-flour, apple juice, dried bean pods and comminuted dried Jerusalem artichoke. The claimed use is for lowering cholesterol levels in animal products. It does not refer to glucosamine generation or presence or use of glucosamine in plant material or final product In WO2003/070168, carrot seeds have been studied for their chemical composition and their activity for the reduction of inflammation-related pain (cycloxygenase enzyme-mediated inflammation). It does not refer to glucosamine generation or presence or use of glucosamine in carrot raw material or extract or isolated compounds.

Industrial Sources of Glucosamine

Industrial glucosamine is a pure compound obtained from the acidic hydrolysis of chitin from shellfish, a complex carbohydrate derived from N-acetyl-D-glucosamine. Glucosamine can also be produced from enzymatic hydrolysis of shellfish, microbial fermentation (for example with of corn-derived products).

Patents have been filed protecting fermentation processes (thus micro organisms) leading to the production of glucosamine. All these processes concern the production of pure, extracted glucosamine, in competition with shellfish extracts.

As an example, U.S. Pat. No. 6,486,307 describes an improved method for chitin acidic hydrolysis: A method of producing glucosamine hydrochloride from chitin by grinding the chitin to a very fine size and digestion with concentrated hydrochloric acid.

U.S. Pat. No. 6,372,457 describes a method and material for producing glucosamine by fermentation of a genetically modified microorganism.

U.S. Pat. No. 5,998,173 describes a novel process for directly producing N-acetyl-D-glucosamine from chitin utilizing an ensemble of the chitinase family of enzymes to hydrolyse chitin of crustacean shells.

SUMMARY OF THE INVENTION

The present invention relates to a natural, non-animal, and nonmicroorganism derived source of glucosamine i.e. the first intrinsically enriched plant species in glucosamine, said glucosamine is used in the preparation of ingredients/food/feed/pet food products preventing osteoarthritis and/or cosmetic products improving skin quality, the invention also relates processes to reach high glucosamine content from plant materials.

Accordingly, in a first aspect the invention relates to a process for generating glucosamine from plants wherein fresh plants or plant extract are dried at a temperature below 110° C., preferably 92° C. or below for less than one week, preferably between 5 and 50 h.

In a second aspect, the invention relates to the use of glucosamine from plant origin generated through the drying process of the invention in the manufacture of food, feed, pet food or cosmetic products allowing the prevention, treatment and/or alleviation of metabolic disorders of the osteo-articular tissues and/or the maintenance of joint health in mammals and/or allowing the improvement of the skin quality and the prevention or restoration of age-related alterations of skin in mammals.

In a third aspect, the invention relates to an orally ingestible food or pet food composition or cosmetic composition containing glucosamine generated from plant materials through a drying process.

DETAILED DESCRIPTION OF THE INVENTION

Surprisingly, we have now found that glucosamine can be formed during the controlled drying process of some raw plant materials.

In the present specification, the word "pet" has to be understood as comprising dogs, cats, rabbits, guinea pigs, mice, rats, birds (for example parrots), reptiles and fish (for example goldfish). However, the term also includes other domesticated animals, such as livestock, for example, cattle, horses, pigs, sheep, goats, buffaloes, camels, and the like. Horses for example are known to suffer from OA.

In the present specification, by "orally ingestible composition" it has to be understood any composition that can be ingested by mammals, including humans or pets. It encompasses nutritional supplements, medicines, pills, tablets, nutritionally complete diets, as well as any type of usual food products, such as, for example, confectionery, pastries, milk-containing products, cereals, biscuits, sugar-based and fat-based confectionery products, drinks, liquid compositions and the like.

These compositions can be nutritive, and therefore provide calories and nutrients, or can be cosmetic, and in this case provide few calories but have an effect on the skin, hair and/or nails, for example. Cosmetic compositions that correspond to the present definition of "orally ingestable compositions" can be in the form of pills, tablets, liquides or granules, for example.

In the present specification, by "cosmetic composition", it has to be understood any composition that can be applied topically, on the skin, hair and/or nail. For example, it can be in the form of a gel, or ointment, a salve, a lotion, a spray, a bandage, a cream, a balm, a milk or a foaming product.

In the present specification, by "free glucosamine", it has to be understood non-polymerized glucosamine.

In the present specification, by "high amount of glucosamine" it has to be understood that the amount of glucosamine is higher than traces of glucosamine, and higher than the amounts in the corresponding fresh (non-dried) material. It should be understood as glucosamine present in amounts above 150 mg per kg dry matter of raw material, preferably above 700 mg per kg dry matter of raw material, and most preferably above 1000 mg per kg dry matter of raw material.

In the present specification, by "plant" or "derived plant extract" it has to be understood any plant material capable of generating glucosamine according to the drying process of the invention, and any type of plant extract capable of generating glucosamine according to the drying process of the invention from said plant material by any extraction procedure known to the skilled person.

Accordingly, in an aspect, the present invention describes new sources of glucosamine from plants through a drying process in order to develop an orally ingestable composition or cosmetic ingredients from plant material processed to contain intrinsically free glucosamine, acting as preventive, curative and/or alleviative agent of osteoarthritis in the acute and chronic forms and generally of all pathological conditions originating from metabolic disorders of the osteo-articular tissue and maintenance of joint health in mammals, and improving skin quality and preventing or restoring age-related alterations of skin in human or animal.

With respect to the first object of the present invention, the plant or derived-plant extract are processed (dried) according to the invention in order to contain natural free glucosamine in high amount.

The "orally ingestible composition" or "cosmetic composition" comprises as an active ingredient an effective amount of at least one plant raw material selected and processed for its content in glucosamine, or plant extract, or pure glucosamine derived from the said plant raw material or mixture of glucosamine and other compounds issued from the said plant raw material.

In a preferred embodiment, the plant or plant extract is from any part of the plant, e.g. leaves, tubers, fruits, seeds, roots, grains or cell cultures. After controlled drying process of the plant raw material, the plant or plant extract may be in the form of a dried, lyophilised extract of leaves, roots and/or fruits depending on the source of plant, or fresh plant, or glucosamine-enriched fraction.

The plant or derived-plant extract is selected for its ability to generate free glucosamine through the drying process of the present invention; in particular it may be selected from the group consisting of plant species containing sucrose, fructose or inulin such as *Cichorium*, *Daucus*, *Helianthus*, *Beta*.

In a most preferred embodiment the plant or plant-extract may be for example root of Chicory (*Cichorium intybus*), carrot (*Daucus carota*), tuber of Jerusalem artichoke (*Helianthus tuberosum*), root of beet (*Beta vulgaris*).

It is well known that such plant species are used in various forms for food and/or pet food applications. Nevertheless, it does not concern nor a food or pet food composition nor a cosmetic composition containing glucosamine generated from plant materials through the drying process as set forth in the present invention.

The drying process of the present invention is, according to the inventors, the only way to increase/obtain glucosamine at high levels from plants. Accordingly, through the drying processes used in the present invention, the quantities of glucosamine obtained are higher than 500 mg per kg dry matter of chicory root, than 100 mg per kg dry matter of carrot root, or than 50 mg per kg dry matter of Jerusalem artichoke tubers or beet root. The process of the present invention is a drying process: the plant material is harvested, cut and dried in an oven or in an industrial dryer at a temperature below 110° C., preferably between 80 and 105° C., most preferably 92° C. or below for less than one week, preferably between 5 and 50 h depending on the plant species and plant organ. Although not wishing to be bound by theory, we believe that it is preferable to cut the plant material in slices or cubes, preferably having a maximum width of 5 cm. The inventors indeed believe that it is important for the present invention in order to reach optimised thermodynamic exchanges.

Still not wishing to be bound by theory, we also believe that glucosamine is not coming from the direct degradation of macromolecules with the subsequent release of free glucosamine, but is likely due to the release of free fructose and amino acids during the drying of the plant material, following by the first steps of a Maillard reaction. The mechanism of the Maillard reaction is complex. However, it is generally divided into three stages:

(1) The first stage involves the sugar-amine condensation and the Amadori rearrangement. No browning occurs at this stage.

(2) The second stage involves sugar dehydration and fragmentation, and amino acid degradation via the Strecker reaction especially at high temperatures, as used in candy manufacture, for example at the end of this stage, there is a beginning of flavor formation-depending on which flavor is studied.

(3) Formation of heterocyclic nitrogen compounds. Browning occurs at this stage.

The present invention may report specific conditions allowing the first step of the formation of the reaction chain, leading to accumulate glucosamine through Heyns/Amadori reactions. Specifically during the first step, it is known that ketoses, such as fructose, react with amines to form aminoaldoses, (Heyns reaction). The intermediates to this reaction are imines. Aminoaldoses are not very stable and readily react forming the Amadori compound.

The course of the reaction is strongly affected by factors that influence the different chemical reactions involved. These are: temperature and duration of heating, pH and presence of weak acids and bases, water content, type of reactant, amino acid to sugar ratio and oxygen.

The plant or derived-plant extract according to the invention may be used in the preparation of a food composition without further treatment or extraction. The said composition may be in the form of a nutritionally balanced food or pet food, a dietary supplement, a treat or a pharmaceutical composition.

In one embodiment, an orally ingestable composition for human consumption is prepared. This composition may be a nutritional complete formula, a dairy product, a chilled or shelf stable beverage, a soup, a dietary supplement, a meal replacement, a nutritional bar or a confectionery product, for example.

In another embodiment, an orally ingestable composition for human or pet cosmetics is prepared. This composition may be in the form of pills, tablets, liquids and/or granules, among others Apart from the plant or derived-plant extract according to the invention, the nutritional formula may comprise a source of protein. Dietary proteins are preferably used as a source of protein. The dietary proteins may be any suitable dietary protein; for example animal proteins (such as milk proteins, meat proteins and egg proteins); vegetable proteins (such as soy protein, wheat protein, rice protein, and pea protein); mixtures of free amino acids; or combinations thereof. Milk proteins such as casein, whey proteins and soy proteins are particularly preferred. The composition may also contain a source of carbohydrates and a source of fat.

If the nutritional formula includes a fat source, the fat source preferably provides about 5% to about 55% of the energy of the nutritional formula; for example about 20% to about 50% of the energy. The lipids making up the fat source may be any suitable fat or fat mixtures. Vegetable fats are particularly suitable; for example soy oil, palm oil, coconut oil, safflower oil, sunflower oil, corn oil, canola oil, lecithins, and the like. Animal fats such as milk fats may also be added if desired.

A source of carbohydrate may be added to the nutritional formula. It preferably provides about 40% to about 80% of the energy of the nutritional composition. Any suitable carbohydrate may be used, for example sucrose, lactose, glucose, fructose, corn syrup solids, and maltodextrins, and mixtures thereof. Dietary fibre may also be added if desired. If used, it preferably comprises up to about 5% of the energy of the nutritional formula. The dietary fibre may be from any suitable origin, including for example soy, pea, oat, pectin, guar gum, gum arabic, and fructooligosaccharides. Suitable vitamins and minerals may be included in the nutritional formula in an amount to meet the appropriate guidelines.

One or more food grade emulsifiers may be incorporated into the nutritional formula if desired; for example diacetyl tartaric acid esters of mono- and di-glycerides, lecithin and mono- and di-glycerides. Similarly, suitable salts and stabilisers may be included.

Vitamins and minerals may also be combined with the plant or derived-plant extract.

The nutritional composition may be enterally administrable; for example in the form of a powder, tablet, capsule, a liquid concentrate, solid product or a ready-to-drink beverage. If it is desired to produce a powdered nutritional formula, the homogenized mixture is transferred to a suitable drying apparatus such as a spray drier or freeze drier and converted to powder.

In another embodiment, a nutritional composition comprises a milk-based cereal together with a prebiotic formulation. Preferably, the milk-based cereal is an infant cereal, which acts as a carrier for the prebiotic formulation.

In another embodiment, a usual food product may be enriched with at least one plant or derived-plant extract according to the present invention. For example, a fermented milk, a yoghurt, a fresh cheese, a renneted milk, article of confectionery, for example a sweet or sweetened beverage, a confectionery bar, breakfast cereal flakes or bars, drinks, milk powders, soy-based products, non-milk fermented products or nutritional supplements for clinical nutrition.

The amount of the plant or derived-plant extract in the composition may vary according to the plant source and its utilization. In a preferred embodiment, an efficient daily dose amount is of at least about 1 mg, and more preferably from 1 mg to 1500 mg of the active molecule per day, and more preferably around 200 mg for a 15 kg dog.

The plant or derived-plant extract according to the invention may be used in the preparation of a pet food composition. The said composition may be administered to the pet as a supplement to its normal diet or as a component of a nutritionally complete pet food. It may also be a pharmaceutical composition.

The plant or derived-plant extract may be used alone or in association with other plants such as vegetables, tea, cocoa, or with other bioactive molecules such as antioxidants, fatty acids, prebiotic fibers, chondroitin sulphate among others.

Glucosamine may be first extracted from the plant material, alone or jointly with other compounds such as inulin or fructooligosaccharides (FOS).

Preferably, the pet food composition comprises about 0.01 to 0.5 g (1 to 50%) of dry plants per gram of dry pet food for a 15 kg dog; and 0.001 to 0.1 g (0.1 to 10%) of dry plants per gram of wet pet food for a 15 kg dog.

The nutritionally complete pet food composition according to the invention may be in powdered, dried form, a treat or a wet, chilled or shelf stable pet food product. These pet foods may be produced by ways known in the art. Apart from the plant or derived-plant extract, these pet foods may include any one or more of a starch source, a protein source and a lipid source.

The choice of the starch, protein and lipid sources will be largely determined by the nutritional needs of the animal or the human, palatability considerations, and the type of product applied in pet food and for elderly pets, the pet food preferably contains proportionally less fat than pet foods for younger pets for example. Furthermore, the starch sources may include one or more of rice, barley, wheat and corn.

The pet food may optionally also contain a prebiotic, a probiotic microorganism or another active agent, for example a long chain fatty acid. The amount of prebiotic in the pet food is preferably less than 10% by weight. For example, the prebiotic may comprise about 0.1% to about 5% by weight of the pet food.

For pet foods, which use chicory as the source of the prebiotic, the chicory may be included to comprise about 0.5% to about 10% by weight of the feed mixture, more preferably about 1% to about 5% by weight.

If a probiotic microorganism is used, the pet food preferably contains about $10^4$ to about $10^{10}$ cells of the probiotic microorganism per gram of the pet food; more preferably about $10^6$ to about $10^8$ cells of the probiotic microorganism per gram. The pet food may contain about 0.5% to about 20% by weight of the mixture of the probiotic microorganism; preferably about 1% to about 6% by weight; for example about 3% to about 6% by weight.

If necessary, the pet food is supplemented with minerals and vitamins so that they are nutritionally complete. Further, various other ingredients, for example, sugar, salt, spices, seasonings, flavouring agents, and the like may also be incorporated into the pet food as desired.

For dried pet food, a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food before processing. A suitable process is described in European patent application No 0850569. If a probiotic microorganism is used, the organism is preferably coated onto or filled into the dried pet food. A suitable process is described in European patent application No 0862863.

For wet food, the processes described in U.S. Pat. Nos. 4,781,939 and 5,132,137 may be used to produce simulated meat products. Other procedures for producing chunk type products may also be used; for example cooking in a steam oven. Alternatively, emulsifying a suitable meat material to produce a meat emulsion, adding a suitable gelling agent, and heating the meat emulsion before filling into cans or other containers may produce loaf type products.

Administering to a human or animal, the food or pet food composition as described above, results in an improved joint health. This food composition helps to prevent osteoarthritis in pets, humans, and horses, which results in a better activity or mobility of the individual.

The cosmetic composition comprising glucosamine from plant origin comprises compounds known to the skilled person of the cosmetic field. It can furthermore be associated with other active compounds such as retinol, vitamin A, liposomes, vegetal DNA and/or RNA, elastase inhibitors collagen, collagenase inhibitors, oils, moisturisers, antioxidants, vitamin C, polyphenols, silicone, among others.

The cosmetic composition of the invention is useful for retarding the aging process of skin as well as diminishing the aging process effects, mainly by having an action on elasticity and moisture through the action of glucosamine on MMPs. The anti-aging effect is also treated and/or prevented by an action on collagen.

In another aspect, the present invention relates to the use of glucosamine from plant origin for the effects mentioned above.

In still another aspect, the invention relates to a method for the treatment, alleviation and/or prophylaxis of osteoarthritis in humans, pets or horses, comprising the step of using an individual, a composition as described above.

In addition, it further relates to a method for improving skin quality and preventing or restoring age-related alterations of skin comprising the step of using an individual, a composition as described above.

EXAMPLES

The following examples are illustrative of some of the products and methods of making the same falling within the scope of the present invention. They are not to be considered in any way limitative of the invention. Changes and modifications can be made with respect to the invention. That is, the skilled person will recognise many variations in these examples to cover a wide range of formulas, ingredients, processing, and mixtures to rationally adjust the naturally occurring levels of the compounds of the invention for a variety of applications.

Example 1

Chicory Intrinsically Enriched in Free Glucosamine

Drying

After harvest, 200 g (fresh weight) roots of chicory (*Cichorium intybus*) are cut in slices of 1×1 cm, and then dried in an oven at a temperature of 92° C. for 50 h. Raw (fresh) material as well as commercial dried chicory roots (Leroux company, France) are extracted and analysed too.

Analysis:

Extraction of Glucosamine:

2 g of ground and specifically dried chicory root are extracted with 20 ml of water at room temperature for 1 minute. The solution is filtered on filter Schleicher & Schultz (n°597) or centrifuged. A purification step of the solution is performed using a cation exchange column (Oasis cartridge WATERS, MCX type, ref. 186 000 776). Basic compounds entrapped on the matrix are eluted with MeOH/NH$_4$OH 2% (v/v). After filtration, an aliquot is used for direct injection on LC system (DIONEX).

Separation:

Analysis is carried out with a HPAE/PED system using an ion exchange PA1 column (4*250 mm) with DIONEX DX 500 apparatus.

Programme:

| ELUTION (%) | | | | |
|---|---|---|---|---|
| Time (min) | H$_2$O | 0.1M NaOH | 0.25 NaOH | Comment |
| 0 | 85 | 15 | 0 | Balancing |
| 60 | 85 | 15 | 0 | |
| 60.1 | 0 | 0 | 100 | Washing |
| 70 | 0 | 0 | 100 | |
| 70.1 | 85 | 15 | 0 | Balancing |
| 90 | 85 | 15 | 0 | |

Flow: 1 ml/min. Volume of injection: 20 μl. Standard: Glucosamine from Sigma (ref: G4875).

In these conditions, glucosamine has a retention time of round 11 min and is easily detected for further quantification in chicory extracts properly processed. A concentration of 900 mg/kg dry weight has been quantified by this method in the present example, instead of less than 10 mg/kg without drying process or in commercial dried roots of chicory.

Confirmation of the Presence of Glucosamine:

In order to confirm the presence of glucosamine in chicory plant extracts, three different qualitative techniques have been evaluated.

Thin Layer Chromatography (TLC)

Pure glucosamine and plant extracts were analysed on HPTLC (High Performance Thin Layer Chromatography) silica gel plates (Merck, ref. 1.05642) with Ethyl acetate/MeOH/water (50/50/10; V/V/V) as eluant. After elution, the plates are sprayed with an acetic acid solution of ninhydrine 1% and heated at 120° C. for 10 min. One spot appeared in a pink/blue color at the same rate factor (Rf) for the reference and extracts.

Chemical Degradation

In the presence of ninhydrine, an oxidative de-amination occurs with glucosamine, which leads to the release of arabinose easily detected through routine sugar LC analysis. Presence of arabinose with control and chicory extracts was unambiguously confirmed.

Derivatization of Glucosamine

Reverse phase chromatography using pre-column derivatization with phenylisothiocyanate and UV detection ($\lambda$=254 nm) was used with the pure compound and plant extracts as described by Zhongming et al.: "Determination of nutraceuticals, glucosamine hydrochloride in raw materials, dosage form and plasma using pre-column derivation with UV HPLC. In J. of Pharmaceut. and Biomed. Analysis, 1999 (20), 807-814."

The corresponding peak of derivatized glucosamine was detected in chicory extracts as well as with pure compound.

Example 2

Carrot Enriched in Free Glucosamine 70 g (fresh weight) of carrot roots are cut in slices of 1×1 cm then dried in an oven at a temperature of 91° C. for 7 h, then 10 h at 40° C. Extraction and analysis are performed as in example 1, leading to a glucosamine concentration of 190 mg/kg dry weight, instead of less than 1 mg/kg without drying process.

Example 3

Dry Pet Food with Chicory

A feed mixture is made up of about 58% by weight of corn, about 5.5% by weight of corn gluten, about 22% by weight of chicken meal, 2.5% chicory roots previously dried according to the process described above (example 1), salts, vitamins and minerals making up the remainder.

The feed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to dogs. The pieces are then dried to a moisture content of about 1% by weight.

This dry dog food has a positive effect on cartilage health and increases their mobility.

Example 4

Wet Canned Pet Food with Supplement

A mixture is prepared from 73% of poultry carcass, pig lungs and beef liver (ground), 16% of wheat flour, 2% of dyes, vitamins, and inorganic salts. This mixture is emulsified at 12° C. and extruded in the form of a pudding, which is then cooked at a temperature of 90° C. It is cooled to 30° C. and cut in chunks. 45% of these chunks are mixed with 55% of a sauce prepared from 98% of water, 1% of dye, and 1% of guar gum. Tinplate cans are filled and sterilised at 125° C. for 40 min.

As a supplement to be mixed with the pet-food before serving, additional packaging (e.g. sachet) contains 25 g of powdered carrot or chicory or Jerusalem artichoke or beet roots parts, previously dried according to the process described above (examples 1 and 2), to be added to the daily food. The corresponding amount for the pet is about 25 g/day and this can be supplied as a supplement with (e.g. on top of) the can.

The invention claimed is:

1. An orally ingestible composition or cosmetic composition for treating osteoarthritis and arthritis, wherein said composition is in a form selected from the group consisting of food products, beverages, nutritional supplements, medicines, pills, tablets, nutritionally complete diets, gels, ointments, salves, lotions, sprays, bandages, creams, balms, milks, foaming products, and combinations thereof comprising a fat source and at least one plant material comprising an effective amount of processed *Helianthus*, wherein said processed *Helianthus* contains glucosamine in an amount greater than 150 mg/kg dry matter, and wherein the processed *Helianthus* is obtained from raw *Helianthus* plant material processed by a drying process at a temperature between 80° C. and 92° C. between 5 and 50 hours to obtain glucosamine in an amount greater than 150 mg/kg dry matter.

2. A skin or hair care product comprising an effective amount of a fat source and at least one plant material comprising processed *Helianthus* containing glucosamine in an amount greater than 150 mg/kg dry matter, wherein the processed *Helianthus* is obtained from raw *Helianthus* plant material processed by a drying process at a temperature between 80° C. and 92° C. between 5 and 50 hours to obtain glucosamine in an amount greater than 150 mg/kg dry matter.

3. An orally ingestible composition for treating osteoarthritis and arthritis, wherein said composition comprises a source of protein and at least one plant material comprising an effective amount of processed *Helianthus* containing glucosamine in an amount greater than 150 mg/kg dry matter, the wherein said processed *Helianthus* is obtained from raw *Helianthus* plant material processed by a drying process at a temperature between 80° C. and 92° C. between 5 and 50 hours to obtain glucosamine in an amount greater than 150 mg/kg dry matter.

4. The orally ingestible composition or cosmetic composition of claim 1 further comprising milk proteins.

5. The orally ingestible composition or cosmetic composition of claim 1 further comprising at least one of inulin or fructooligosaccharides.

6. The orally ingestible composition or cosmetic composition of claim 1 further comprising chondroitin sulfate.

7. The orally ingestible composition or cosmetic composition of claim 1 wherein the at least one raw plant material is subjected to lyophilization.

* * * * *